(12) United States Patent
Tsironis (10) Patent No.: US 10,591,511 B1
(45) Date of Patent: Mar. 17, 2020

(54) FREQUENCY ADJUSTABLE PRE-MATCHING COAXIAL TRANSISTOR TEST FIXTURE

(71) Applicant: Christos Tsironis, Dollard-des-Ormeaux (CA)

(72) Inventor: Christos Tsironis, Kirkland (CA)

( * ) Notice: Subject to any disclaimer, the term of this patent is extended or adjusted under 35 U.S.C. 154(b) by 254 days.

(21) Appl. No.: 15/848,475

(22) Filed: Dec. 20, 2017

Related U.S. Application Data (60) Provisional application No. 62/436,722, filed on Dec. 20, 2016.

(51) Int. Cl.
*G01R 1/04* (2006.01)
*G01R 1/20* (2006.01)
*G01R 31/26* (2020.01)

(52) U.S. Cl.
CPC ........... *G01R 1/203* (2013.01); *G01R 1/0408* (2013.01); *G01R 31/2601* (2013.01)

(58) Field of Classification Search
CPC .. G01R 1/203; G01R 1/0408; G01R 31/2601; G01R 31/31924; G01R 31/2886; G01R 31/2889; G01R 1/30; B23H 7/04
See application file for complete search history.

(56) References Cited

U.S. PATENT DOCUMENTS

| 6,414,563 | B1 | 7/2002 | Tsironis | |
| 10,001,521 | B1 * | 6/2018 | Tsironis | G01R 1/045 |

OTHER PUBLICATIONS

"Test Fixture for Medium and High Power RF Transistors", Product Note 7, Focus Microwaves, Jan. 1994.
"Load Pull", [online], Wikipedia [Retrieved on Nov. 18, 2016] Retrieved from Internet <URL: http://en.wikipedia.org/wiki/Load_pull>.
"MLTF, a Minimum Loss Transistor Test Fixture", Product Note 54, Focus Microwaves, 1999.

* cited by examiner

*Primary Examiner* — Patrick Assouad
*Assistant Examiner* — Suresh K Rajaputra (57) ABSTRACT

Coaxial microwave transistor test fixtures provide lowest insertion loss possible and include, as part of the input and output sections, transformer networks in form of single stage $\lambda/4$ segments bringing (pre-matching) the system $50\Omega$ load closer to the conjugate internal impedance of power transistors. The transforming networks are flat, cylindrical or have oval or elliptical cross sections and have adjustable length, thus operating optimally for transistors with varying optimum frequency and internal impedance and/or capacitive or inductive impedance part. The change in length is done without affecting the overall fixture geometry and structure. The fixtures can be calibrated using standard TRL method.

6 Claims, 11 Drawing Sheets

FREQUENCY ADJUSTABLE PRE-MATCHING COAXIAL TRANSISTOR TEST FIXTURE

PRIORITY CLAIM

This application claims priority on provisional application 62/436,755, titled: Frequency Adjustable Coaxial Transistor Test Fixture, filed on Dec. 20, 2016.

CROSS-REFERENCE TO RELATED ARTICLES

1. TSIRONIS, U.S. Pat. No. 6,414,563, "Low-Loss Microwave Device Test Fixture with Adjustable Blocks".
2. "Test Fixture for Medium and High Power RF Transistors", Product Note 7, Focus Microwaves, January 1994.
3. "Load Pull", [online], Wikipedia [Retrieved on Nov. 18, 2016] Retrieved from Internet <URL: http://en.wikipedia.org/wiki/Load_pull>.
4. "MLTF, a Minimum Loss Transistor Test Fixture", Product Note 54, Focus Microwaves, 1999.

BACKGROUND OF THE INVENTION

This invention relates to high frequency transistor test fixtures used in testing RF transistors in microwave frequencies (see ref. 1, 2). Active RF components (transistors—DUT) need to be thoroughly tested at the operation frequencies before used in amplifier and other circuit designs. "Load pull" and "Source pull" (see ref. 3) are test methods which use impedance tuners to systematically characterize the DUTs under various load and source impedance conditions. Load pull or source pull are automated measurement techniques used to measure Gain, Power, Efficiency and other characteristics of the DUT, employing, beyond source and load impedance tuners, also other test equipment, such as signal sources, directional couplers, test fixtures to house the DUT and input and output power meters (FIG. 1), see ref. 3. Typical test fixtures used are based on micro-strip (FIG. 2) or coaxial (FIG. 3) transmission line structure.

Microstrip test fixtures (FIG. 2) include grounded input (22, 213) and output (28, 215) body sections and a DUT INSERT (214). The DUT (210) is mounted on the INSERT (214) using screws (26) or other securing mechanism. The fixture has input (20) and output (27) connectors and microstrip lines (29, 212) between the connectors. The microstrip lines comprise a dielectric layer on which a thin copper conductor layer is etched using photolithographic process. The DUT (210) package has leads (24, 211) which can be soldered or pressed on the microstrip (29, 212). A coaxial test fixture (FIG. 3) has two slabline sections made of the blocks (25), the cover (10) and the center conductors (31) which lead from the coaxial connectors, which are mounted on the vertical walls (11), to the DUT, which is mounted on the INSERT (21) using vertical studs or screws. The DUT leads are inserted in slots of the center conductors.

BRIEF DESCRIPTION OF THE INVENTION

Figure 5:
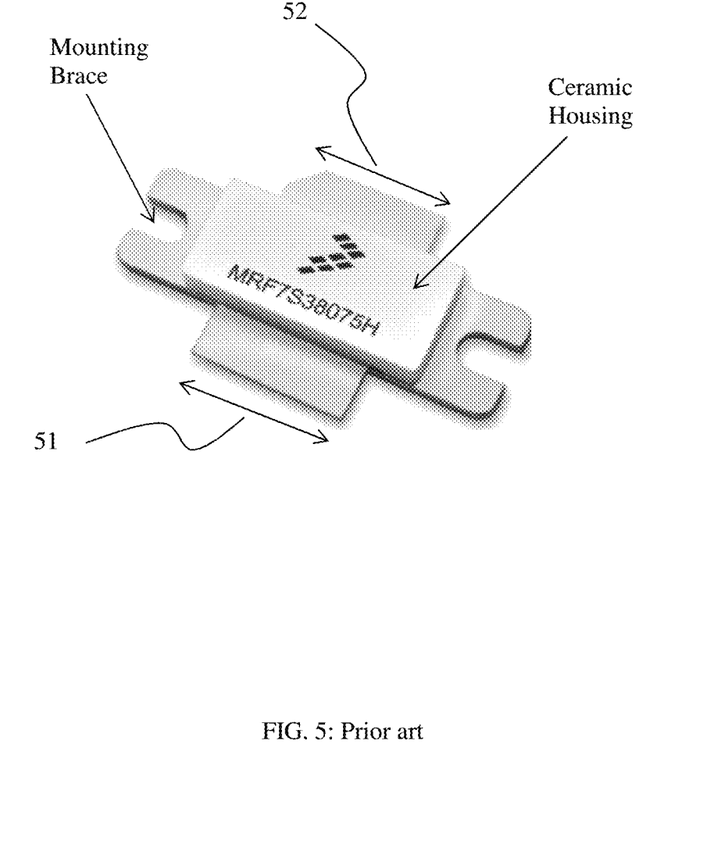
FIG. 5 depicts prior art, a packaged RF power transistor.

High power high frequency transistors have very low input and output impedance, of the order of 1 to 3n. For proper load pull testing, the tuners must conjugate match these impedances. However the tuning range of the tuners is reduced by the insertion loss of the test fixtures; therefore the requirement for extremely low loss test fixtures. Most existing microstrip fixtures (FIG. 2) have non-negligible insertion loss due to the used dielectric material on which the microstrip lines (212, 29) are etched photo lithographically. Since air has the lowest insertion loss of any transmission media, it is logical to make and use airlines, in a coaxial structure, instead of micro-strip. In 2000/2002 such a fixture was disclosed (see ref. 1). This fixture has 50Ω transmission airlines (31, 47, 48) which are not the optimum solution for matching low impedance targets (DUT), both from RF reflection and from mechanical points of view; as shown in FIG. 5 the transistor leads (51, 52) are wide and should best also be mechanically matched to the adjoining center conductors. This leads to the requirement of a pre-matching test fixture, i.e. a test fixture which comprises a section of low characteristic impedance slabline, between the DUT and the 50Ω section, as an intermediate step between 50Ω and 1-3Ω of the transistor internal impedance.

Figure 6:
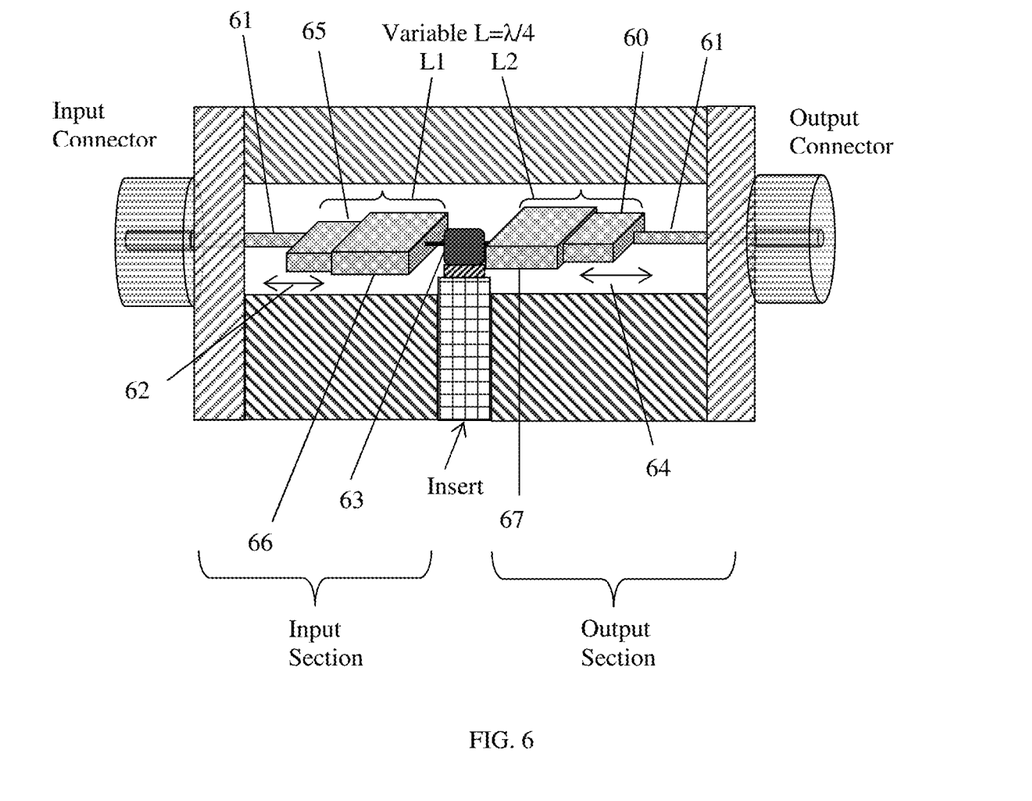
FIG. 6 depicts a pre-matched coaxial test fixture using quarter lambda transformer sections with adjustable length.
Figure 7:
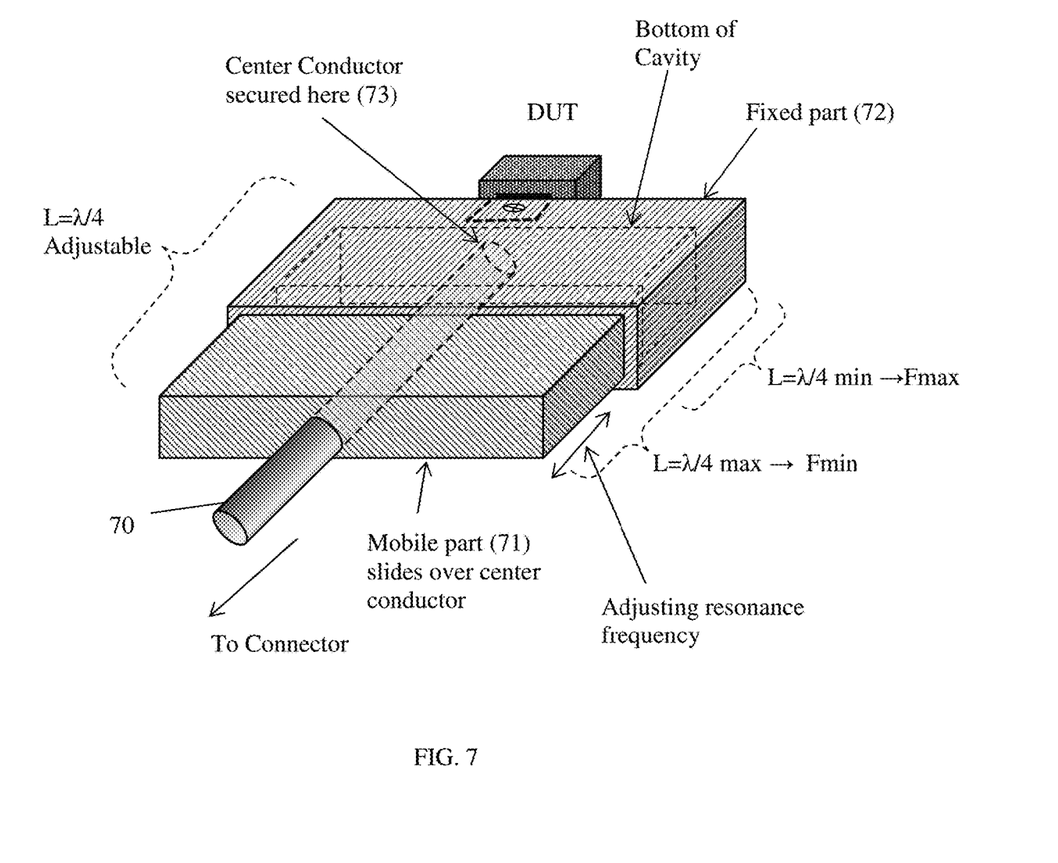
FIG. 7 depicts 3D view of adjustable transforming segment attached to a transistor.

The pre-matching sections are, in general, single intermediate impedance sections equal or close to $\lambda/4$ long. This means they are resonant and changing operation frequency requires physical replacement of sections of center conductor. This invention discloses a new embodiment of a high frequency coaxial fixture, whereby the transmission airline comprises sections having characteristic impedance Z1 different than 50Ω; in fact by widening the center conductor (48) one can reach Z1<50Ω or, by narrowing it, one can reach Z1>50Ω, depending on the internal impedance of the DUT to be matched. In the present embodiment we concentrate on lowering Z1, i.e. increasing the cross section of the center conductor. The general rule applies that when a transmission line section with length $L=\lambda/4$ with a characteristic impedance Z1 is attached to a transmission line with a characteristic impedance Zo (typically 50Ω), then on the other side of the transmission line section with characteristic impedance Z1 one sees an impedance $Z2=Z1^2/Zo$. As an example: if Z2=10Ω, then the transforming section must have a characteristic impedance of Z1=22.36Ω. The $\lambda/4$ transforming section resonates at Fres (GHz)=75/L(mm), whereby L is the physical length of the transforming section (FIGS. 6 and 7). This invention discloses transforming segments with adjustable length and thus adjustable resonance frequency. Hereby resonance frequency is the frequency at which an open section of transmission line turns from capacitive to inductive as shown by point (113) in FIG. 11.

BRIEF DESCRIPTION OF THE DRAWINGS

The invention and its mode of operation will be better understood from the following detailed description when read with the appended drawings in which:

FIG. 2A through 2B depict prior art.

FIG. 4A through 4B depict prior art.

FIG. 9A through 9B depict the overall adjustable wideband transforming structure.

FIG. 10A through 10C depicts views of transforming sections.

DETAILED DESCRIPTION OF THE INVENTION

Figure 1:
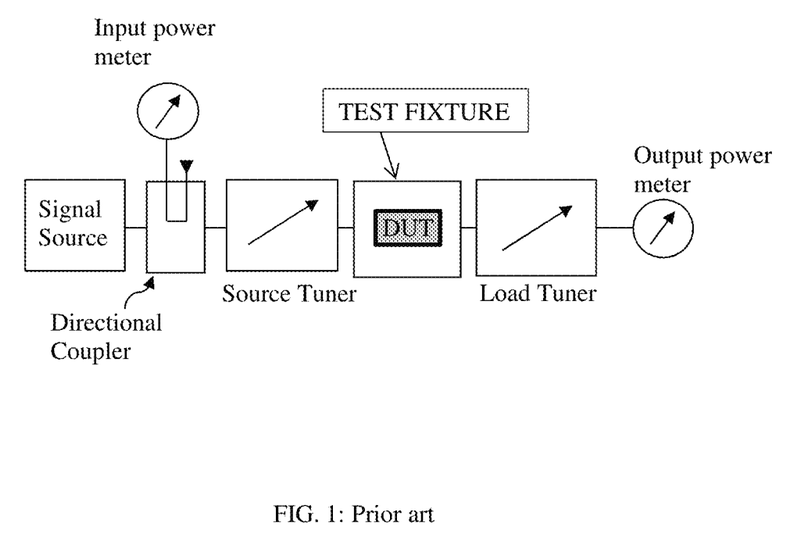
FIG. 1 depicts prior art, a traditional load pull measurement setup.
Figure 2A:
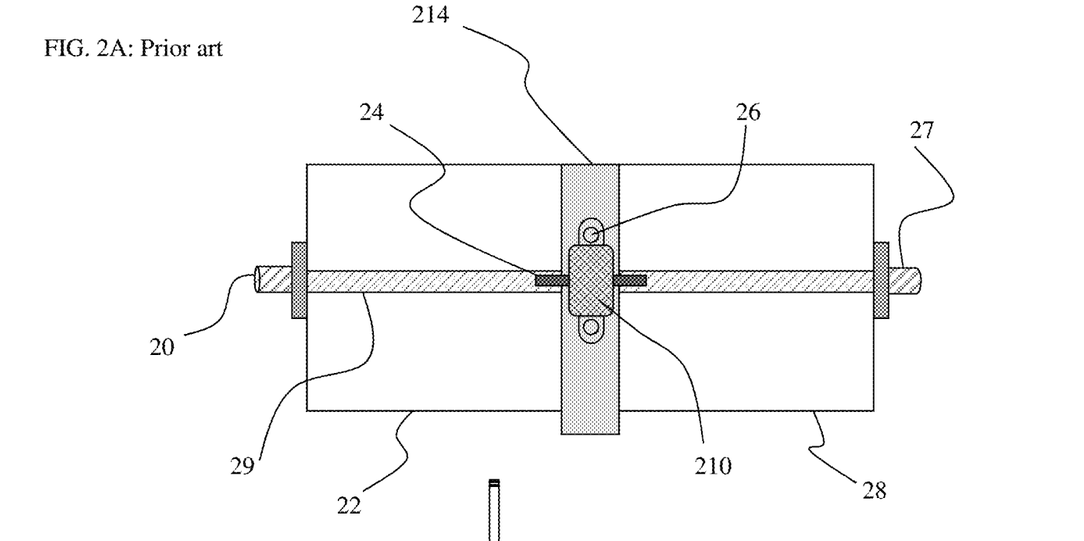
FIG. 2A depicts top view of a micro-strip transistor test fixture.
Figure 2B:
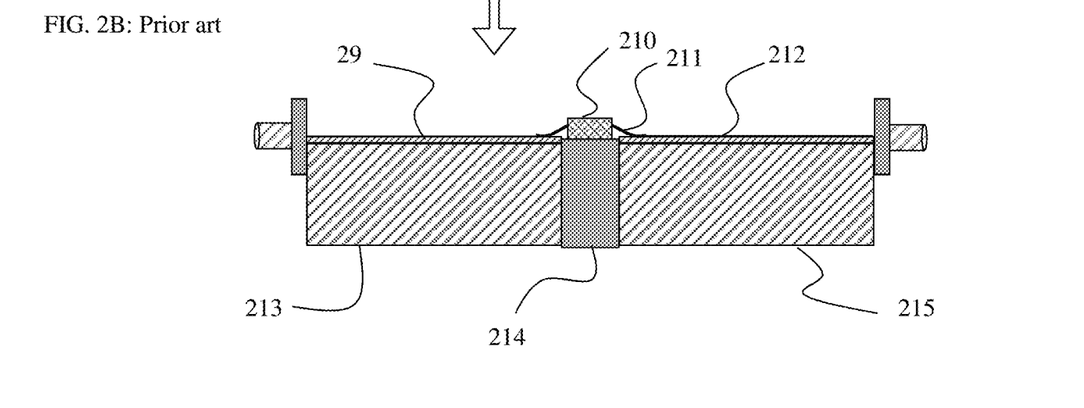
FIG. 2B depicts side view of the micro-strip transistor test fixture.
Figure 3:
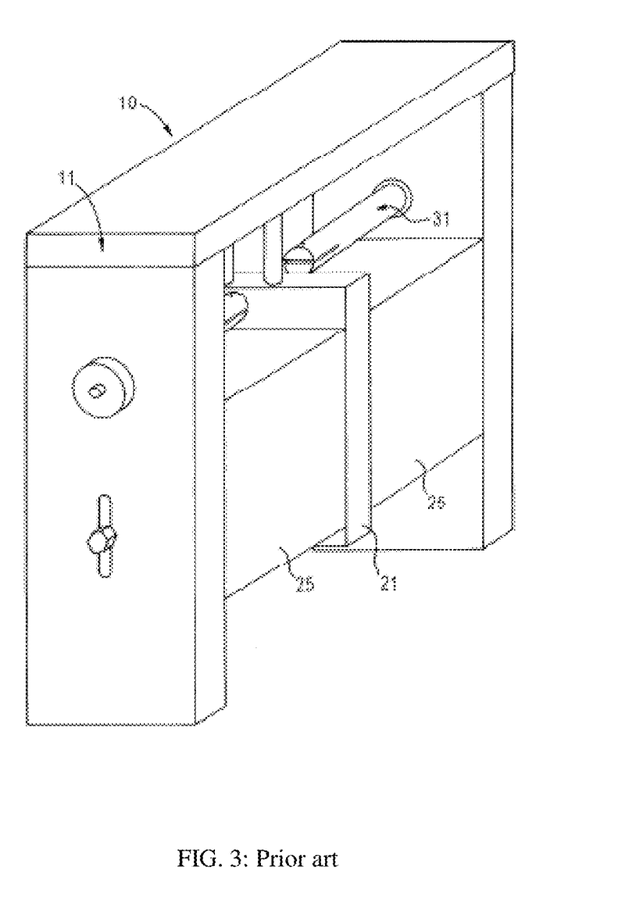
FIG. 3 depicts prior art, a 3D view of coaxial 50Ω test fixture (see ref. 1).
Figures 4A, 4B:
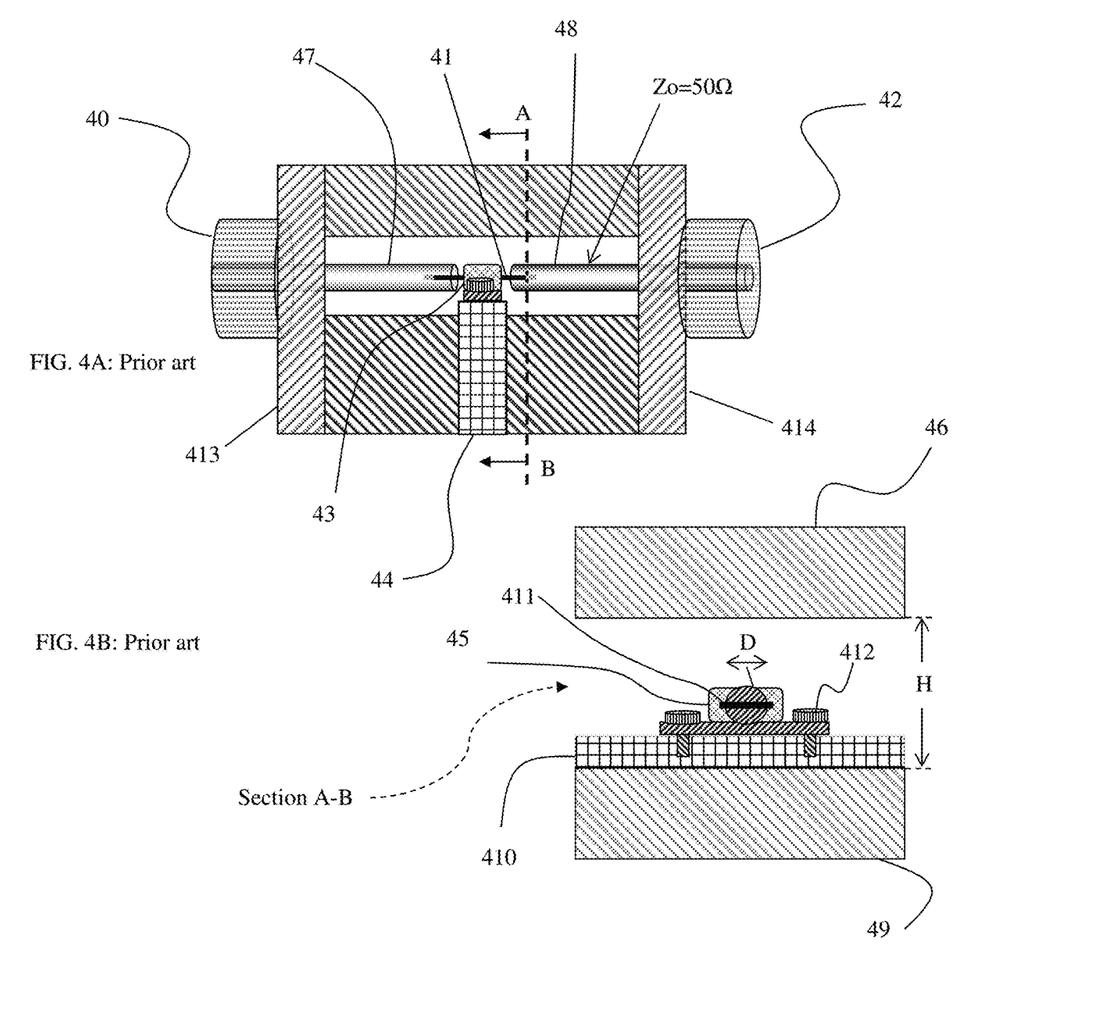
FIG. 4A depicts side view of 50Ω coaxial test fixture.
FIG. 4B depicts view of cross section "A-B" of the 50Ω coaxial test fixture.

FIGS. 3 and 4 show the prior art coaxial transistor test fixture (see ref. 1 and 4). Two coaxial connectors (40, 42) are attached to vertical walls (413, 414) and the extensions of the center conductors (31, 47, 48) of the connectors form with the two blocks (25, 49) and the metallic cover (11, 46) form an open transmission line (slabline), which is interrupted in the center to insert a block (21, 44, 410), referred to hitherto as "INSERT", which carries the packaged DUT (43). In this case the transistor package (43, 45) is firmly secured on the INSERT (44) which is part of the horizontal slabline structure. The signal enters in the input port (40) and leaves at the output port (42) and is conducted to the transistor by the two coaxial center conductor segments (47, 48). The transistor leads (41) are inserted into horizontal slots (411) of the center conductors. The test fixture INSERT (44, 410) holds the transistor package (43, 45) with two screws (412) for good RF grounding and heat dissipation. The advantage of this type of test fixture is lower insertion loss between the transistor leads (41) and the input (40) and output (42) ports and by consequence it allows for the tuning range of the tuners to be transferred to the DUT with less loss (FIG. 1).

Figure 10A:
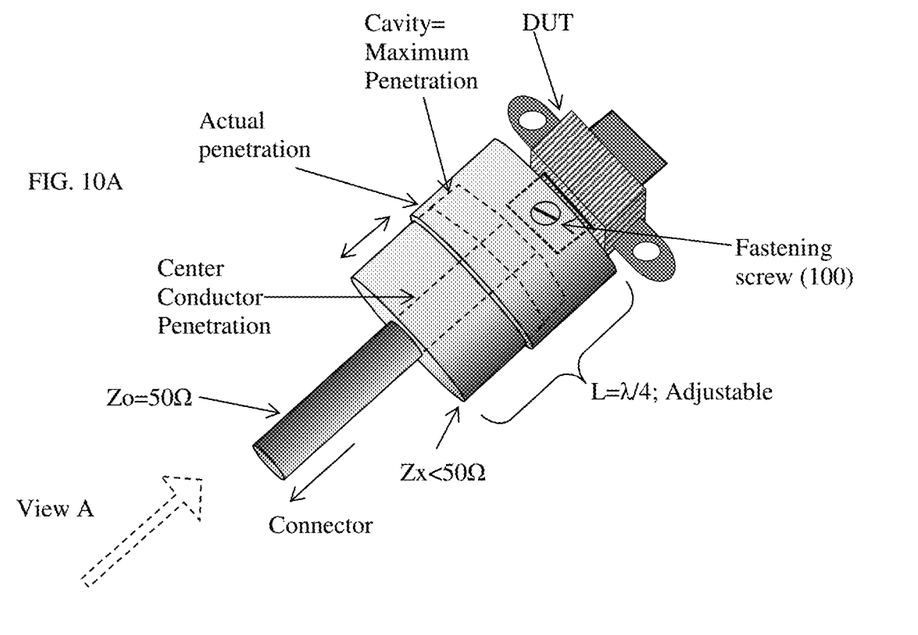
FIG. 10A depicts 3D view of a transistor mounted in length-adjustable cylindrical or ellipsoid transforming segment of coaxial transistor test fixture.
Figures 10B, 10C:
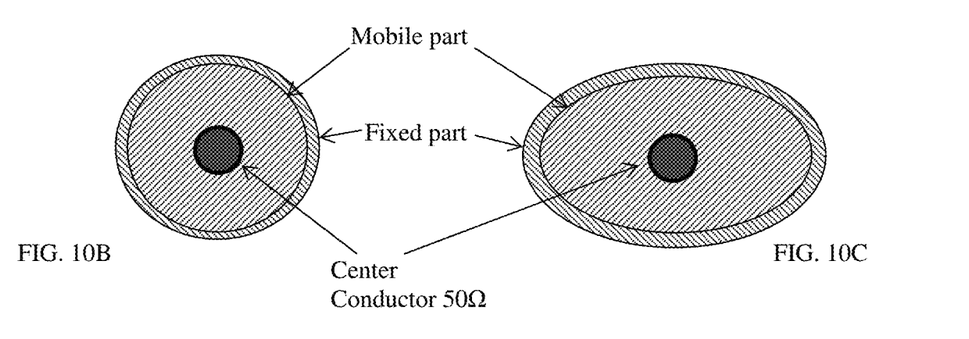
FIG. 10B depicts view A of cross section of cylindrical transformer.
FIG. 10C depicts view A of cross section of ellipsoid transformer.

In a fixed frequency embodiment of a coaxial pre-matching RF (radio frequency) test fixture the impedance transformers are sections of center conductor having a physical length of one quarter wavelength (L=λ/4) and create characteristic impedance Z1 lower than 50Ω in the slabline (FIGS. 7 and 10). These sections can be cylindrical, ellipsoid (FIG. 10) or parallelepiped (FIG. 7). Electromagnetic analysis determines the correct dimensions ("diameter" in case of cylinders FIG. 10, and "width×thickness" in case of parallelepipeds, FIG. 7 or ellipsoids also in FIG. 10). Typically, in a 20 mm wide (H, FIG. 4B) slabline structure, a cylindrical center conductor of 11 mm diameter creates Zo=50.3Ω and a center conductor of 17 mm diameter a characteristic impedance of 24.2Ω. A parallelepiped (rectangular section) center conductor of 17 mm width and 5 mm thickness creates a Zo of 50.6Ω and a 13 mm×7 mm center conductor a Zo of 21Ω in the same slabline. Ellipsoid dimensions lie between the these extremes. It is therefore possible to adjust the characteristic impedance of the transforming sections to electrically match the DUT impedance and to mechanically match the width of the package leads (51, 52) as well. Both these structures allow for the axial length of the transforming segments to be adjustable in order to create a frequency change, as shown in FIGS. 6, 7 and 10.

Figure 11:
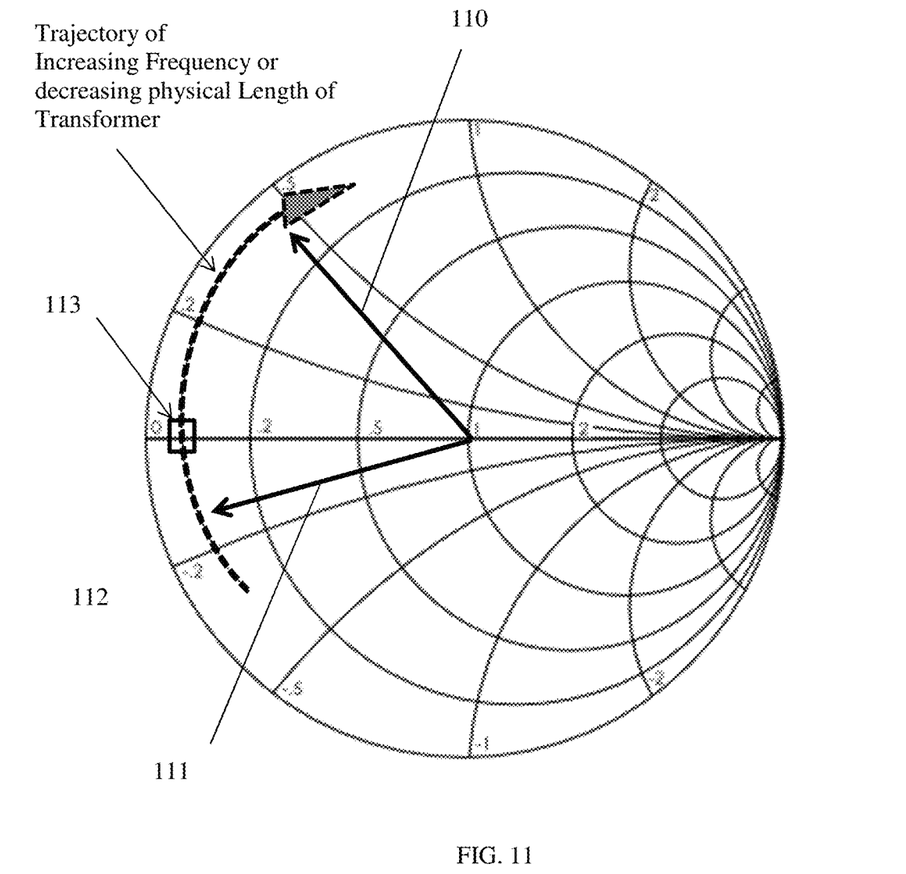
FIG. 11 depicts frequency response of reflection factor (impedance) presented to DUT by the adjustable transforming segment. Control parameter is decreasing physical length or increasing frequency.

In FIG. 6 the overall fixture is shown with both transforming segments individually adjustable: movable core blocks (65) and (60) slide (62, 64) inside fixed blocks (66, 67), thus adjusting the actual physical length of the non-50Ω transforming segments to L=L1 and L=L2, which connect to the input and output connectors via the center conductors (61). As can be seen in FIG. 11 the reflection factors (110, 111, 112), presented to the DUT, rotate with changing frequency and associated physical length (in air physical equals electrical length). Therefore by adjusting the physical length of the input (L1) and the output (L2) transforming segment independently one can account for different phase of the input and output internal impedance of the DUT (63) to be matched simultaneously.

Figure 8:
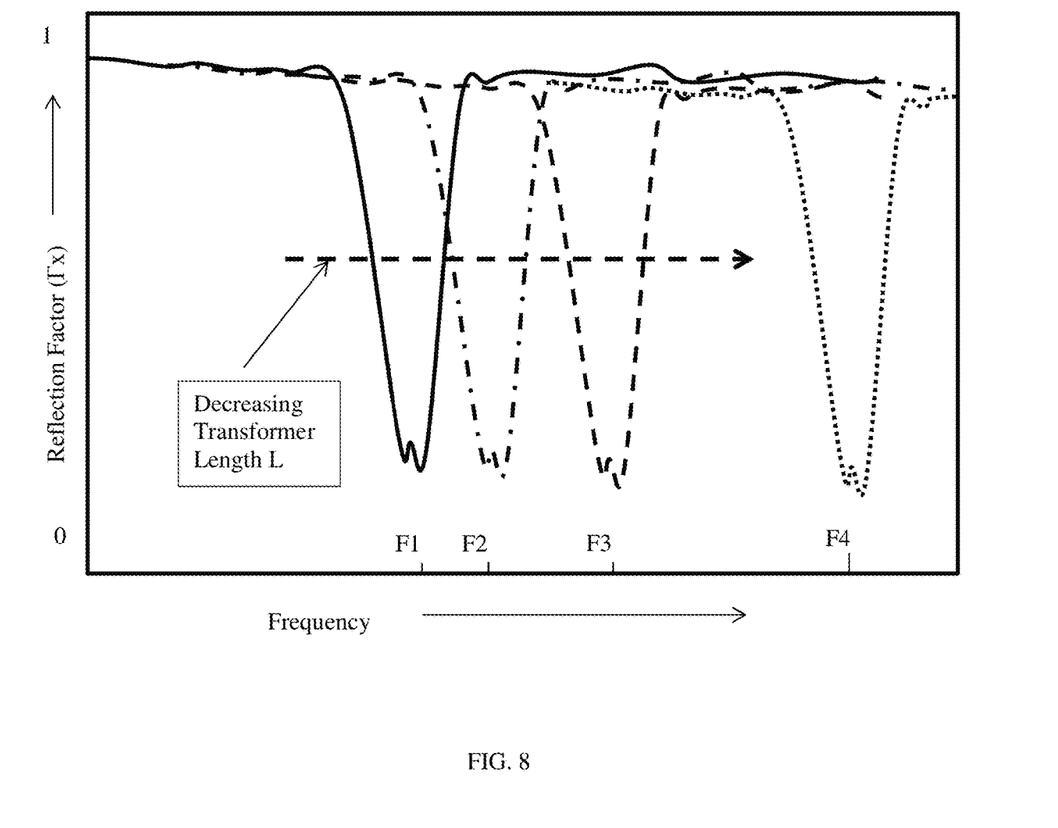
FIG. 8 depicts the frequency response of the reflection factor of the pre-matching sections of the test fixture when terminated with the low internal impedance of the DUT when decreasing the length of the quarter wavelength transformer and by that increasing the resonance frequency from F1 to F2 to F3 . . . .

A detailed layout of one transforming, non-50Ω, segment is shown in FIG. 7. One can see the movable block (71) penetrating and sliding inside the fixed housing block (72), while also sliding on the center conductor (70); the sliding between the two blocks and the center conductor shall be RF safe, i.e. without interruptions; the center conductor traverses the cavity of the fixed block and is secured against the bottom on the far end of the cavity of the fixed housing block (72). As the mobile block (71) penetrates inside the fixed block, the overall axial physical length L of the transformer changes, and so does its resonance frequency (FIG. 8). When the movable block is fully inserted the overall length of the fixed housing part is λ/4 minimum and creates a resonance at the maximum frequency Fmax. When the movable block (71) is extracted to the maximum still safe from RF point of view position, without leaving a gap between the two blocks, the length of the transforming section is a maximum and creates a minimum resonance frequency Fmin. Either frequency can be calculated by the relation F=75 (GHz)/L(mm).

Due to basic mechanical limitations (FIG. 9B) the extractable length of the movable core part (91) must be smaller than the length of the housing part (92), therefore the overall length cannot be doubled. A realistic extension ratio is 1.8, accounting for the necessary overlap (98) at the mouth of the housing and the thickness of the wall at the bottom (99) of the cavity. Therefore the frequency control one realistically can expect is a factor of 1.8 (i.e. from 2 GHz to 3.6 GHz, or from 4 GHz to 7.2 GHz etc.).

As an example, if the fixed block has a length of L=20 mm and the mobile block has a length of 17.5 mm and is fully inserted (leaving typically 2.5 mm in the bottom of the cavity) the resonance frequency will be Fmax=3.75 GHz; if the mobile block is fully extracted, leaving 2.5 mm for RF contact overlap (98), then the total length of the transforming section becomes L=35 mm and the resonance frequency is Fmin=2.14 GHz. During this operation the DUT is securely attached to the fixed block of the non-50Ω transforming segment.

Figure 9A:
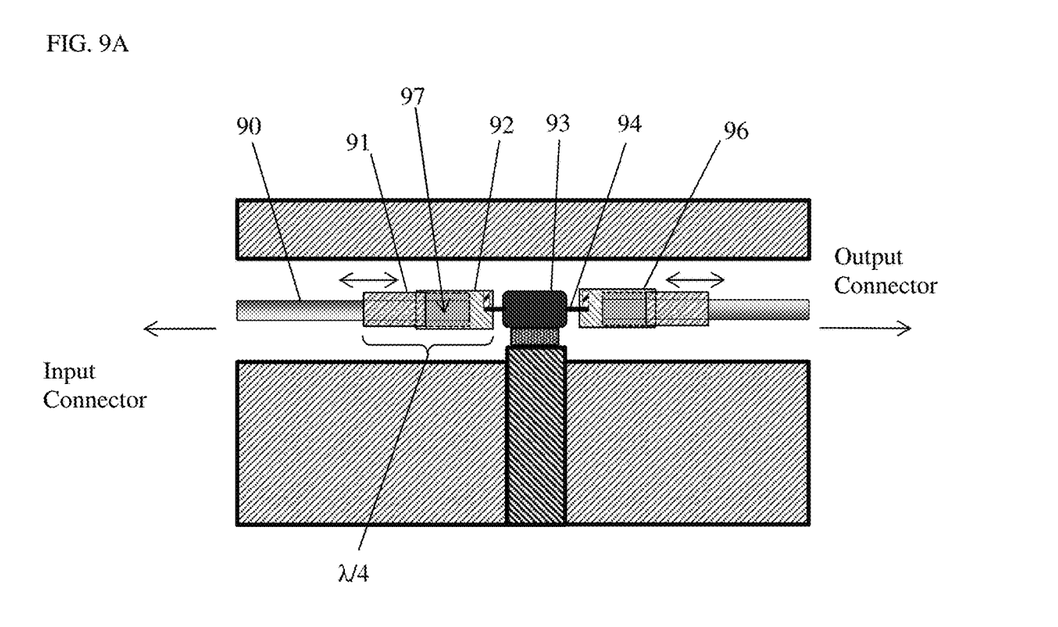
FIG. 9A depicts overall view and FIG. 9B depicts detail of the mechanism of the mobile part sliding over the center conductor and into the cavity of the fixed λ/4 transformer segment.
Figure 9B:
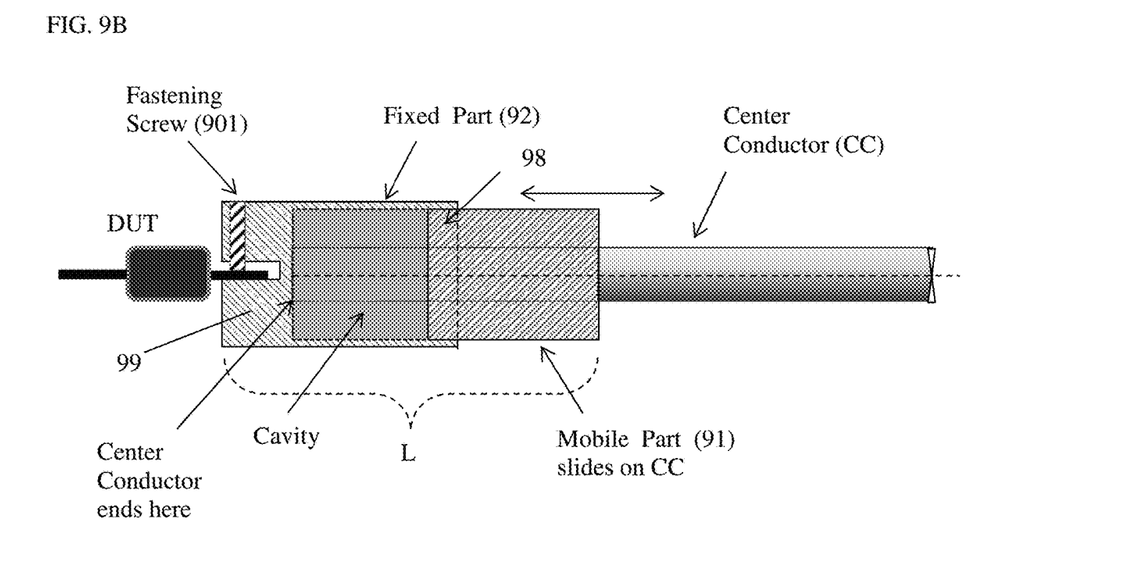

Further representation of the adjustment mechanism is shown in FIG. 9A and in more detail in FIG. 9B. The DUT (93) is secured on the fixed transforming blocks (92, 96) of the transforming segments using its leads (94) and fastening screws (901). The axial physical length of the transforming (non-50Ω) segments is adjusted by inserting or extracting the movable block (91) into and from the cavity of the fixed block (92). The movable block slides on the center conductor (90) which also guides the movable block (91) safely sliding into the cavity (97) of the fixed block (92) forming a transforming segment of total length L, which creates a resonance frequency when L=λ/4, keeping in mind that at a frequency F, the free space wavelength is λ/4 (mm)=75/F (GHz). Using single stage λ/4 transformers is narrowband (see FIG. 13); it works best at the specific frequency F1, F2, F3 . . . in gigahertz, Fi(GHz)=75/L(mm), whereby L is the length of the transforming section in millimeters (FIG. 8). When L changes so does Fi change proportionally.

In FIG. 10 the same concept is shown for cylindrical (circular cross section) or ellipsoid (elliptic or oval cross section) transforming segments. All relations and limitations of the parallelepiped (flat) segments of FIG. 7 apply also to the cylindrical or ellipsoid segments of FIG. 10. Whereas parallelepiped (flat) and cylindrical structures are easier to manufacture, structures with elliptical or oval cross sections allow less width than flat transforming structures and more gap towards the metallic walls of the fixture's cover and ground than cylindrical transforming segments, while offering more core material (meat) in the body of the transforming segment to secure the fastening screws (901, 100) than flat transforming segments.

It can easily be seen that the transforming (non-50Ω) segments can be exchanged without changing the structure of the test fixture. This is easily understood, since the fixed part (72) can be mounted, secured and disassembled from the center conductor (70) using a simple thread or fitting hole cut into the bottom body of the housing (73) and the moving part (71) only slides of the center conductor (70) and, in fact, also defines and secures the position of the housing part (72) inside the slabline of the fixture. By replacing the actual non-50Ω segment with one of different "width×thickness" geometry or different diameter, one can generate different characteristic impedance, as described before.

Although the present invention has been explained hereinabove by way of a number of preferred embodiments pertaining to frequency adjustability of non-50Ω center conductor segments in coaxial transistor test fixtures, it should be pointed out that other combinations of the described components are possible and, as far as obvious to a person skilled in the art, they shall not limit the scope of the present invention.

What I claim as my invention is:

1. A frequency adjustable, coaxial, pre-matching RF transistor (DUT) test fixture comprising
    an input section attached to input port,
    an output section attached to output port,
    a metallic block (INSERT) inserted between the sections, which said INSERT carries the DUT, and
    a metallic cover extending from the input port to the output port,
    whereby
    the input section and the output section form sections of slablines, each comprising
        a bottom metallic block,
        sections of the metallic cover,
        coaxial connector associated with the corresponding port, and
        center conductor attached to the connector and reaching from the connector to the INSERT,
    and whereby
        at least one of the center conductors comprises a 50Ω segment and a non-50Ω segment, whereby the non-50Ω segment is inserted between the 50Ω segment and the DUT,
    and whereby
        the axial physical length of the non-50Ω segment is adjustable,
    and whereby
        the minimum axial physical length of the non-50Ω segment is one quarter wavelength (λ/4) at the highest resonance frequency.

2. The test fixture of claim 1,
    whereby
        at least one non-50Ω segment comprises a hollow fixed part and a solid mobile part,
    and whereby
        the fixed part comprises an axial cavity open towards the mobile part,
    and whereby
        the mobile part slides on the center conductor and enters into the cavity of the fixed part,
    and whereby
        the center conductor is attached on one side to the coaxial connector and on the other side to the bottom of the cavity of the fixed part,
    and whereby
        the fixed part is attached to the DUT and the mobile part is closest to the connector, and whereby
        the axial length of the fixed part is λ/4 at the highest resonance frequency and the mobile part fits entirely into the cavity of the fixed part.

3. The test fixture of claim 1 or 2,
    whereby
        the fixed and mobile parts of the at least one non-50Ω segment are parallelepipeds,
    and whereby
        the fixed part is hollow and the mobile part is solid.

4. The test fixture of claim 1 or 2,
    whereby
        the fixed and mobile parts of the at least one non-50Ω segment are co-axial cylinders,
    and whereby
        the fixed part is hollow and the mobile part is solid.

5. The test fixture of claim 1 or 2,
    whereby
        the fixed and mobile parts of the at least one non-50Ω segment are co-axial ellipsoids,
    and whereby
        the fixed part is hollow and the mobile part is solid.

6. The test fixture of claim 1, whereby at least one non-50Ω segment is exchangeable.

* * * * *